United States Patent [19]

Nelson

[11] Patent Number: 4,726,362
[45] Date of Patent: Feb. 23, 1988

[54] DOUBLE HINGED KNEE BRACE WITH DOUBLE LEG WRAP

[76] Inventor: Ronald E. Nelson, 405 Sunset La., Cambridge, Minn. 55008

[21] Appl. No.: 913,934

[22] Filed: Oct. 1, 1986

Related U.S. Application Data

[63] Continuation-in-part of Ser. No. 801,589, Nov. 25, 1985, abandoned.

[51] Int. Cl.[4] ............................. A61F 3/00; A61F 5/04
[52] U.S. Cl. .................................. 128/80 C; 128/165
[58] Field of Search ................. 128/80 C, 80 F, 80 R, 128/88, 165

[56] References Cited

U.S. PATENT DOCUMENTS

| | | | |
|---|---|---|---|
| 2,632,440 | 3/1953 | Hauser et al. | 128/80 F |
| 3,463,147 | 8/1969 | Stubbs | 128/80 R |
| 3,786,804 | 1/1974 | Lewis | 128/80 C |
| 4,064,874 | 12/1977 | Valin | 128/80 C |
| 4,144,881 | 3/1979 | Chappell | 128/80 R |
| 4,320,748 | 3/1982 | Racette et al. | 128/80 F |
| 4,379,463 | 4/1983 | Meier et al. | 128/88 X |
| 4,573,455 | 3/1986 | Hoy | 128/80 C |

*Primary Examiner*—Clifford D. Crowder
*Attorney, Agent, or Firm*—Burd, Bartz & Gutenkauf

[57] ABSTRACT

A knee brace and wrap assembly for protecting and stabilizing the knee joint against overextension, twisting, lateral impact, injury associated with immense muscular effort of the leg muscle and particularly the quadriceps, as well as other such trauma as can result from rigorous activity, such as football or skiing. The brace includes upper and lower leg support means secured to the outer sides of the thigh and calf. The support means can be contoured pads connected by a composite hinge assembly having three pivot points such that the pads will rotate relative to one another upon rotation of the knee about an axis that generally follows that of the knee. The composite hinge assembly has first and second fixed members secured to the leg pads, and first and second movable members comprised as hinge plates pivotally connected to each other and to the fixed members. Stop members limit rotation of the hinge assembly in both directions of rotation of the knee to limit rotation of the knee. According to another form of the invention, support means can be comprised of upper and lower wrap assemblies, each having inner and outer elastic wraps for installation on a leg.

19 Claims, 20 Drawing Figures

DOUBLE HINGED KNEE BRACE WITH DOUBLE LEG WRAP

CROSS REFERENCE TO RELATED APPLICATION

This application is a continuation-in-part of application Ser. No. 801,589, filed Nov. 25, 1985 entitled KNEE BRACE, now abandoned.

BACKGROUND OF THE INVENTION

The knee or knee joint is the hinge system at the juncture where the femur and the tibia are connected by a series of ligaments. It is one of the most mobile joints of the body. In normal movement, it can bend through a range of about 150 degrees and can experience limited twisting. The geometric shape of the femur and tibia as they fit together makes the knee stable. One ligament system holding these bones together is the knee capsule consisting of five ligaments forming a sleeve-like connection. Two additional ligaments that occupy the knee joint are called crossed or cruciate ligaments. Quadricep muscles on the thigh power extension of the leg and are connected to the quad tendon, which attaches to the kneecap. The kneecap is attached to the tibia by the kneecap tendon. Stability and mobility of the knee result from this relatively complex design. Almost any knee injury will restrict its normal range of motion. Five places are susceptible to injury. These are the ligaments, the cartilages, the muscles around the knees, the kneecap and the tendons. Possible injuries include sprained ligaments, tears of knee cartilages, fractures of the bone joints, damage to the kneecap and muscle tendons, and contusion and tears of the quad muscles.

Injury occurs as a result of overextension of the knee, or when a large external force is applied to the bent knee or when tremendous muscular force is applied to the knee by the performer, such as an athlete engaged in football, soccer, rugby, lacrosse or the like. When engaging in such activities, it is important to protect the knee against such injury. This is frequently done through the use of protective wraps, knee braces or like devices. Such devices commonly do not provide adequate support and protection to the knee or, if they do, tend to unduly inhibit normal motion of the knee whereby the full potential of the knee is not realized.

SUMMARY OF THE INVENTION

The invention comprises a knee brace and wrap assembly usable to protect the knee joint from injury or to prevent aggravation of preexistent injury. The brace includes leg supports constituted in one form of the invention as a rigid or semirigid thigh pad connected to a rigid or semirigid calf or lower leg pad by a composite hinge assembly. Both leg pads are secured to the leg by suitable wrap or like structure. Alternatively, the leg supports can be comprised of upper and lower leg wraps constructed according to another form of the invention.

Each leg support secures an arm or anchor that extends toward the knee parallel to the leg. First and second hinge plates are pivotally connected together. Each hinge plate is pivotally connected to one of the arms forming a relatively rigid hinge structure with three pivot points. The three-point hinge permits relative rotation of the leg supports about a resultant horizontal axis that will follow the axis of the knee through the range of normal flexure. Stop members associated with the hinge plates inhibit rotation beyond normal flexure limits in the usual direction of rotation and beyond the straight leg position when in the extended position of the leg. The laterally rigid hinge protects the knee from lateral impact, twisting, and other abnormal movement occasioned by exterior force or significant muscular effort on the part of the wearer. The leg supports and hinge assembly prevent extension of the leg at the knee joint.

DESCRIPTION OF PREFERRED EMBODIMENTS

Figure 1:
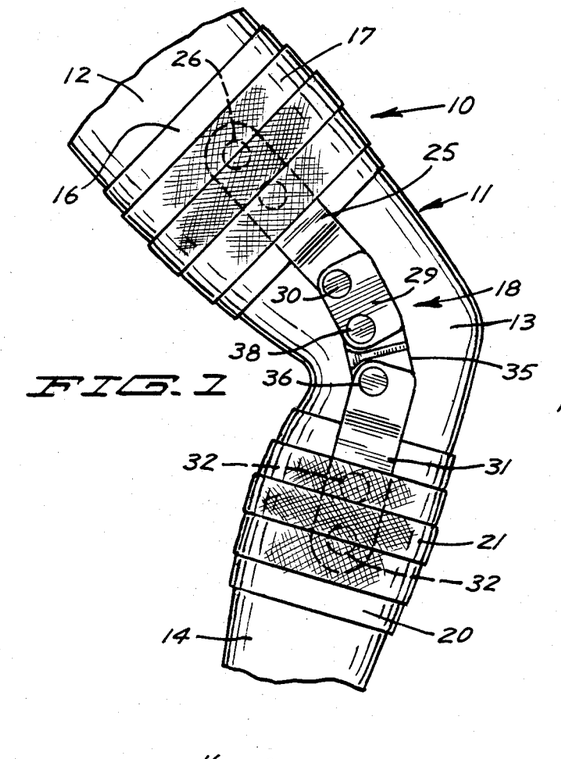
FIG. 1 is a side elevational view of a knee brace according to the one form of the invention installed on a leg.
Figure 2:
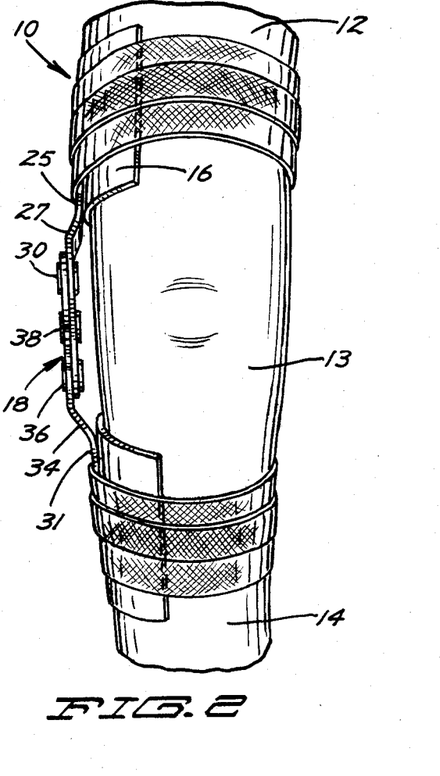
FIG. 2 is a front elevational view of the knee brace and leg of FIG. 1.

Referring to the drawings, there is shown in FIGS. 1 and 2 a knee brace according to one form of the invention indicated generally at 10 installed on a leg 11 spanning a portion of the thigh or upper leg 12, the knee joint 13, and the lower leg or calf 14. Knee brace 10 tends to stabilize the leg 11 and, in particular, the knee joint 13 against undue twisting, overextension, lateral impact and like trauma. Knee brace 10 is comfortable to wear and permits movement of the knee 13 generally throughout its normal range while affording the foregoing protection.

Figure 4:
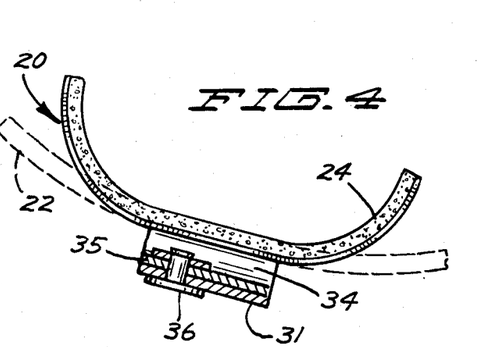
FIG. 4 is a sectional view of a portion of the knee brace of FIG. 3 taken along the line 4—4 thereof.

Knee brace 10 includes an upper leg support or thigh pad 16 securely fixed to the thigh 12 of a wearer by suitable wrap structure 17. A composite hinge assembly 18 connects upper leg support or pad 16 to a lower leg support or lower pad 20 and spans knee joint 13. Hinge assembly 18 can be normally covered by a sleeve or like structure but is shown uncovered for purposes of illustration. Lower leg pad 20 is securely fixed to the lower leg 14 by suitable wrap structure 21. Leg pads 16, 20 are generally C-shaped or contoured to anatomically conform to the engaged limb portion for comfort and security. As shown in FIG. 4, lower leg pad 20 includes a semirigid base 22 having a soft inner liner 24 of material, such as foam rubber. Base 22 can be formed from a flat sheet of thermally formable material, as indicated in phantom in FIG. 4, which when heated can be shaped to the anatomical contour of an individual user. Alternatively, base 22 can be formed in a generally curved shape with sufficient flexibility to be conformable with wrap structure 21 to thighs of different sizes. Upper leg pad 16 can be of similar construction.

Composite hinge assembly 18 has three parallel pivot connections to enable relative rotation of the leg pads about a resultant axis conforming to that of the knee while affording the protection provided by a relatively rigid hinge assembly.

Hinge assembly 18 includes first and second arms or anchor members securely connected to the leg pads, and first and second hinge plates pivotally connected to the arms and to each other. A first anchor member or arm 25 is connected at one end by suitable rivet-type elements 26 to the upper leg pad 16. Arm 25 extends from the leg pad 16 in generally parallel relationship to the upper leg 11 in a direction toward the knee 13. Arm 25 is intermediately outwardly or laterally offset, as at 27 (see FIG. 2) near the lower edge of leg pad 16 to be spaced from the knee. The opposite end of first arm 25 terminates above the knee joint 13 and is connected to a first hinge plate 29 by a first arm pivot pin 30.

A second anchor member or arm 31 is securely connected by rivet-type elements 32 to the side of the lower leg pad 20 and extends from the lower leg pad 20 in a direction toward the knee 13 generally parallel to the lower leg. The second arm 31 is outwardly or laterally offset, as at 34, proximate the upper edge of the leg pad 20 so as to be spaced from the knee 13. The opposite end of the second arm 31 terminates beneath the knee 13 and is connected to the second hinge plate 35 by a second arm pivot pin 36. The first and second hinge plates 29, 35 are pivotally connected by a central pivot pin or hinge plate pivot pin 38, which is located vertically between the other two pivot pins. The arms and hinge plates are relatively rigid members providing a laterally and axially stable construction.

Figures 5, 6, 7:
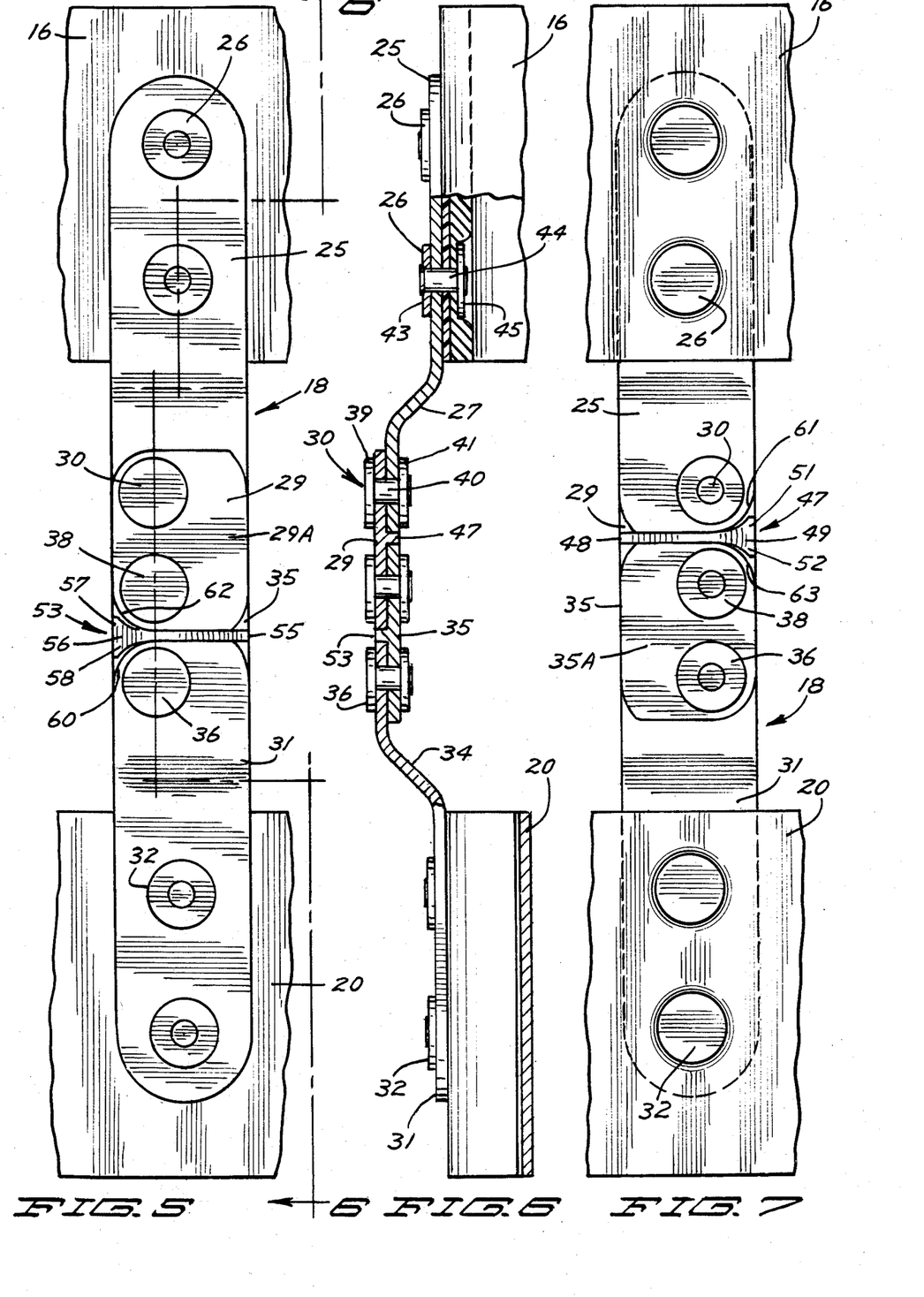
FIG. 5 is an enlarged front plan view of the hinge assembly of the knee brace of FIG. 1.
FIG. 6 is a sectional view of the hinge assembly of FIG. 5 taken along the line 6-6 thereof.
FIG. 7 is a back elevational view of the hinge assembly of FIG. 5.

Detailed construction of composite hinge assembly 18 is shown in FIGS. 5-7 where the first and second arms and hinge plates are shown in relatively linear alignment, as when the leg is in the straight position and the knee joint is unbent. The three pivot pins 30, 36 and 38 are shown in linear vertical alignment although they need not necessarily be in such linear positioning. As shown in FIG. 6, each pivot pin includes a head 39, a shank 40 passing through pivot openings provided in the connected members, and a cap 41 securely fitted on the opposite end of the shank 40. Shank 40 is loose enough in the pivot openings to allow the relative pivotal movement of the connected members. The rivet-type elements 26, 32 holding the arms to the leg pads each include a cap 43 on one side of the pad, a rivet shank 44 passing through a fastener opening in the pad and liner, and a second cap 45 tightly fitted on shank 44 in tight relationship to the first cap with respect to the leg pad.

Outer ends of the arms 25, 31 connected to the hinge plates are flat. The hinge plates 29, 35 are alike in construction and are oppositely facing in assembled relationship shown. Each has a flat proximal face in sliding surface contact with an arm and a portion of the other hinge plate, and a distal face. The first hinge plate has a distal face 29A shown in full view in FIG. 5. As shown in FIGS. 6 and 7, the proximal face of first hinge plate 29 is divided by a pivot stop member comprised as a generally T-shaped rib 47 that has a transverse stem 48 and a head 49. Stem 48 longitudinally divides the proximal surface of the first hinge plate 29, and head 49 is located adjacent a side edge of the hinge plate and points inwardly with respect to the direction of rotation of the knee. Head 49 has inwardly curved shoulders 51, 52 on either side of stem 48.

In like fashion, second hinge plate 35 has a distal face 35A shown in full view of FIG. 7. As shown in FIGS. 5 and 6, the proximal face of second hinge plate 35 is divided by a pivot stop member comprised as a generally T-shaped rib 53 that has a transverse stem 55 and a head 56 at one end of the stem and adjacent an edge of the hinge plate facing interiorly of the direction of rotation of the knee. Stem 55 longitudinally divides the proximal face of hinge plate 35. Head 56 has interior curved shoulders 57, 58 on either side of stem 55.

Confronting edge of the arms and hinge plates cooperate with the ribs 47 and 53 to limit the permitted degree of rotation of the hinge assembly 18 between the straight leg position shown in FIGS. 5-7 and a fully bent position of the knee. Rotation beyond the straight leg position in a direction opposite that of a knee-bend rotation is limited by the stems 48, 55 of the first and second T-shaped ribs 47, 53. As shown in FIG. 7, the downwardly facing outer edge of the first arm 25 abust a corresponding edge of the stem 48, thus inhibiting further rotation of the arm 25 in a counterclockwise direction about the first arm pivot 30. An end edge of the second hinge plate 35 abuts the opposite side of the stem 48 to stop further rotational movement of the second hinge plate 35 with the first hinge plate 28 about the hinge pivot 38 in a clockwise direction, as viewed in FIG. 7. As shown in FIG. 5, the same rotational movement is inhibited by confrontation of the lower edge of the first hinge plate 29 against a side of the stem 55 of the second T-shaped rib 53 on the second hinge plate 35. Finally, the upper edge of the second arm 31 is in confronting relationship with the opposite side of the stem 55, thus to inhibit counterclockwise rotational movement of the second arm 31 with respect to the second hinge plate 35 about the second arm hinge pivot 36 when the two abut, as viewed in FIG. 5.

The various confrontations of the edges of the hinge plates and arms with the sides of the stems of the first and second T-shaped ribs inhibit rotation of the hinge assembly 18 beyond the straight leg position shown in a direction opposite to that of knee bending.

Figure 3:
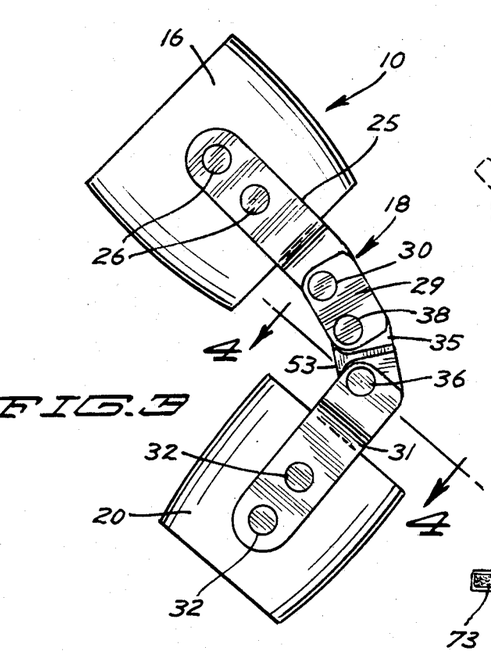
FIG. 3 is a side elevational view of the knee brace of FIG. 1 removed from the leg and without the leg wrapping.

Rotation of hinge assembly 18 in the knee-bend direction is limited by confrontation of curved exterior shoulders on the arms and hinge plates with the interior curved shoulders of the pivot stop members 47, 53. For example, referring to FIG. 5, second arm 31 is in the extreme forwardly rotated position with respect to second hinge plate 35. The upper edge of second arm 31 abuts with the lower surface of stem 55 of rib 53 to prevent further forward rotation between the second arm 31 and the second hinge plate 35. From this position, second arm 31 can rotate with respect to the second hinge plate 35 in a knee-bend direction or clockwise, as viewed in FIG. 5, about the second arm pivot 36. The upper end of arm 31 has a rearward exterior shoulder 60 which faces the lower interior shoulder 58 of rib 53. In the vicinity of the curvature of shoulder 58 of rib 53, the curvature of shoulder 60 corresponds to or is greater that the curvature of the shoulder 58, such that no interference is occasioned between the shoulders upon relative rearward rotation in the knee-bend direction until the predetermined limit of rotation is reached. At this point, the shoulders intercept and further relative rotation between the arm 31 and the second hinge plate 35 is prevented. The shoulders intercept at that point where the shoulder 60 on second arm 31 obtains a small curvature, such that further rotation causes it to intercept a portion of the head 56 of rib 53. This limit of rotation between the second arm 31 and the second hinge plate 35 is shown in FIG. 3 where the shoulders of each are in intercepting or jammed relationship. This occurs at a relative angle of approximately 55 degrees removed from the linear orientation of FIG. 5.

Rotation of the members about the first arm pivot 30 and the hinge pivot 38 is similarly limited. Referring to FIG. 7, the first arm 25 has a rearward exterior lower shoulder 61 in facing but clearing relationship to the interior shoulder 51 of the rib 49. The shoulder 61 has a greater curvature, such that there is no impediment to initial rearward rotation of the first arm 25 relative to the first hinge plate 29, or a clockwise rotation of the arm 25 as viewed in FIG. 7. In FIG. 7, the difference in curvature between the shoulders is emphasized by the gap between them. The relative rotation can continue until the gap is closed and the shoulders intersect or are in a position of confrontation or abutment. This occurs at a relative angle of approximately 55 degrees removed from the linear position shown in FIG. 7.

Relative rotation of the first hinge plate and the second hinge plate is limited by both ribs 47, 53 simultaneously. The first hinge plate 29 has a rearward lower shoulder 62 in confronting relationship to the interior shoulder 57 of the second rib 53 on the second hinge plate 35. In like fashion, the second hinge plate 35 has a rearward upper shoulder 63 in confronting relationship to the lower interior shoulder 52 of the first rib 47. Rotation of the first and second hinge plates about the hinge pivot pin 38 will continue until the respective shoulders intercept and prevent further rotation. This occurs at a relative angle of approximately 55 degrees from the linear orientation shown in FIGS. 5 and 7. In FIG. 3, there is shown a relative rotation of the first arm 25 with respect to the first hinge plate 29, and the first hinge plate 29 with respect to the second hinge plate 35, but to a degree less than the permitted limit or less than the relative rotation of the second hinge plate 35 with respect to the second arm 31.

Figure 8:
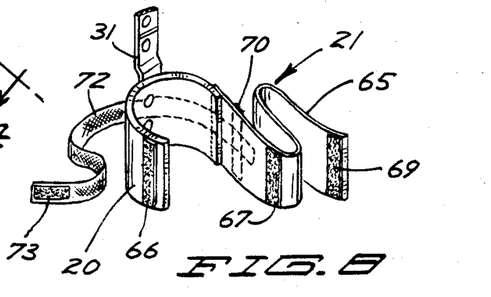
FIG. 8 is a view in perspective showing one of the leg pads of the knee brace of FIG. 1 along with the leg wrap structure.

Various wrap structures are appropriate to hold the leg pads relative to the leg, such as tape, elastic bandages, elastic sleeves or the like. A particular wrap structure 21 is illustrated in FIG. 8 with respect to the lower leg pad 20 and includes an elongate elastic band 65 that is stretchable in a circumferential direction and is fixed to an edge of pad 20. The opposite exterior edge of the leg pad 20 is equipped with a linear strip 66 of fastening material. A second linear strip 67 of fastening material is located on the inside of the elastic band 65 in a position to cover the first strip 66 when the band is wrapped around the leg. The strips 66 and 67 are comprised of synthetic material that adheres when pressed together, such as material of the hook-and-loop variety sold under the trademark Velcro. A third strip 69 is interiorly secured to the free end of the band 65, and a fourth strip 70 is secured near the fixed end of the band 65 in outwardly facing relationship, such that when the remainder of band 65 is wrapped around the leg and the leg pad 20, the free end having the third strip 69 is fastened to the fourth fastening strip 70 near the opposite edge of the leg pad 20. The elastic band is stretched or in tension such to securely hold the leg pad 20 in place. In order to further assist in holding the pad in place, a strap 72 is provided having a free end with a fastening means 73, which can be a buckle or another piece of synthetic material of the type that adheres when pressed together. When the band 65 is stretched around the leg in place, the strap 72 is stretched around in the opposite direction and the free end 73 is fastened to the other side near the fixed end of strap 72.

In use of the knee brace 10, the upper and lower leg pads 16, 20 are positioned on the outside of the leg. The pads can be accurately preformed according to the contour of the individual wearer as previously described, or it can be generally flexible and curved so as to be universally conformable to persons of generally the same stature. Wrap structure 17, 21 is applied to the pads to hold them firmly in place. The wrap structure can be like that shown in FIG. 8. The hinge assembly 18 maintains spatial relationship between the upper and lower leg pads. The plurality of hinge points provided by the hinge assembly 18 permits relative rotation of the upper and lower hinge pads about an axis that corresponds to that of the knee joint and which is the resultant axis of pivoting about the first and second arm pivots and the hinge pivot. Because the resultant pivot axis of hinge assembly 18 is movable, misalignment of the leg pads on the leg with respect to the knee is inconsequential. The hinge assembly 18 protects against lateral blows and twisting. It also holds the leg pads in spaced relationship to prevent overextension of the leg, and the limits provided for pivoting prevent injury caused by rotation beyond the straight leg position or beyond the limited knee-bend position.

Figures 9, 10:
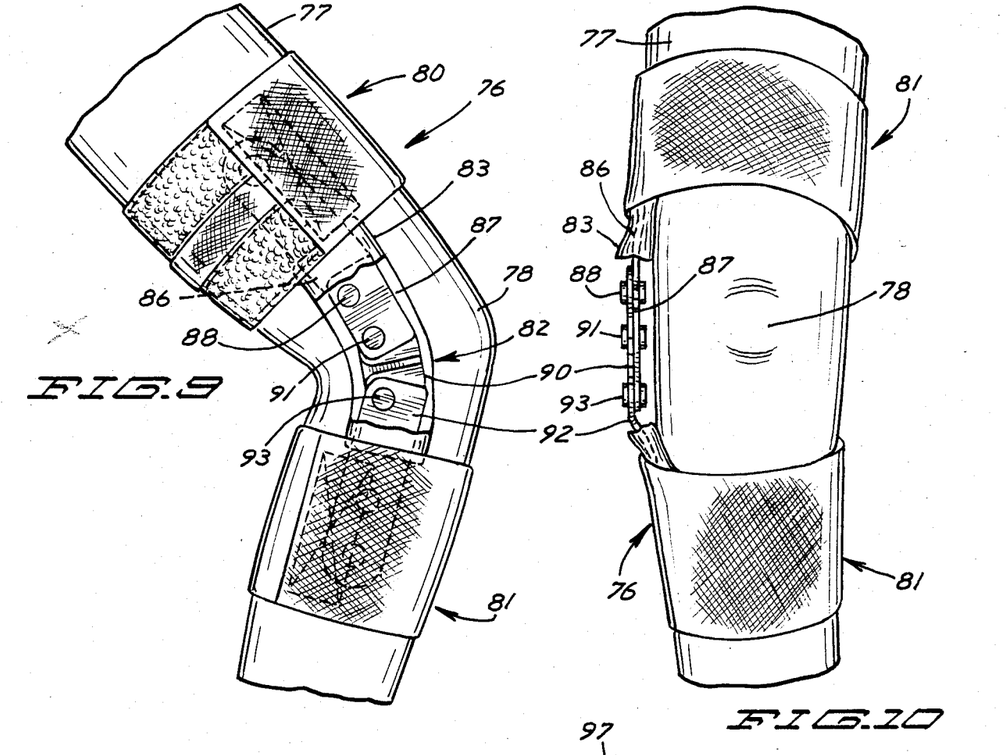
FIG. 9 is a side elevational view of a knee brace according to a second form of the invention installed on a leg.
FIG. 10 is a front elevational view of the knee brace and leg of FIG. 9.

A second form of knee brace according to the invention is indicated generally at 76 installed on a right leg 77 in FIGS. 9 and 10 in spanning relationship to a knee 78. Knee brace 76 includes upper leg engaging support or wrap assembly 80 and a lower leg engaging support or wrap assembly 81 connected by a hinge assembly 82. Hinge assembly 82 can be covered by a pad 83 which is shown broken away in FIGS. 9 and 10 for purposes of illustration.

Hinge assembly 82 is identical in mechanical construction to the earlier described hinge assembly of FIG. 1. A first anchor or arm 85 has an attached end fixed to the upper wrap assembly 80 and extends parallel to the leg toward the knee. The first arm is intermediately offset, as at 86 in FIG. 10 spaced away from the knee. The second end of the first arm is pivotally connected to a first hinge plate 87 by a pivot pin 88. First hinge plate 87 is pivotally connected to a second hinge plate 90 by a second pivot pin 91. A second arm or anchor 92 has a first attached end connected to the second wrap assembly 81. The second end of the second arm 92 is pivotally connected to the second hinge plate 90 by a third pivot pin 93. The first and second hinge plates have T-shaped ribs on opposing faces as earlier described with respect to hinge assembly 18 of knee brace 10 shown in FIGS. 1 and 2. Rotational movement of the knee in both the knee bend and knee-straightening positions is limited by the hinge assembly 82. Hinge assembly 82 presents a relatively rigid structure for stabilizing the knee joint against abnormal movements and providing protection against lateral impact.

Figure 11:
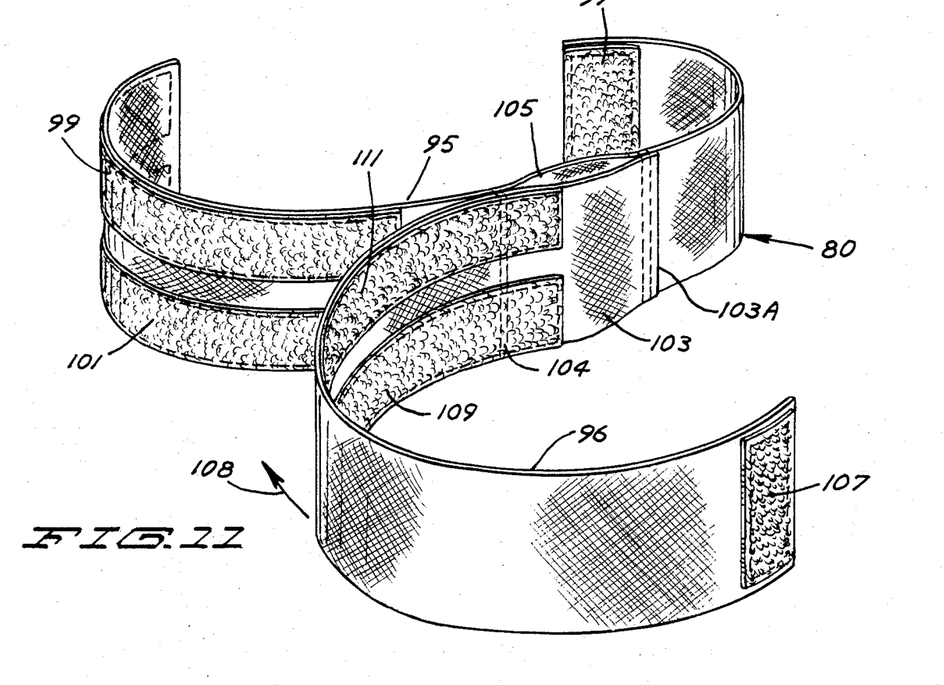
FIG. 11 is a perspective view of a leg wrap assembly of the knee brace of FIG. 9.
Figure 12:
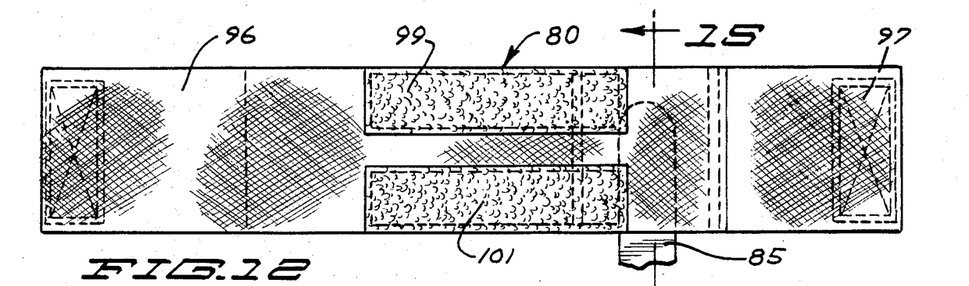
FIG. 12 is a side elevational view of the leg wrap assembly of FIG. 9 showing the distal side thereof.
Figures 13, 14:
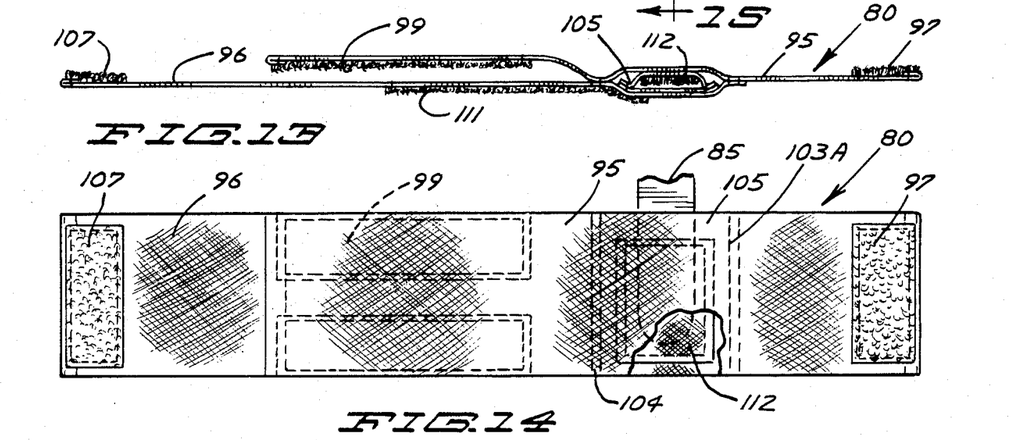
FIG. 13 is a top plan view of the leg wrap assembly of FIG. 12.
FIG. 14 is a side elevational view of the leg wrap assembly of FIG. 12 showing the opposite of proximal side thereof.

Upper and lower wrap assemblies 80 and 81 are alike in construction. FIG. 11 shows wrap assembly 80 in perspective view without the end of the first arm 85 attached thereto, and FIGS. 12 through 14 show top and planned views of wrap 80 with the end of arm 85 in place. As shown in FIG. 11, wrap assembly 80 includes an inner or proximal wrap 95 and an outer or distal wrap 96. Each wrap is made of a suitable length of circumferentially or longitudinally elastic material to permit stretching in a circumferential direction as it is wrapped around the leg. One end of the interior wrap 95 carries vertical adhering or fastening strip 97 that faces inwardly with respect to the leg. The other end of the interior wrap 95 carries a pair of parallel outwardly facing horizontal adhering or fastening strips 99, 101. The adhering strips 97, 99 and 101 are formed of synthetic material of the type that adheres when pressed together, such as that sold under the trademark Velcro. The horizontal strips 99, 101 are outwardly facing with respect to the leg so as to be in confronting relationship with the first adhering strip 97 when overlapping. The horizontal length of the second adhering strips 99, 101 permits adjustment of wrap 95. The horizontal adhering strips 99, 101 can be elastic for extension with the wrap 95.

Outer wrap 96 has one end 103 fixed to the exterior of inner wrap 95 at an intermediate location thereon, as by stitching 103A. A second segment of the outer wrap 96 is fixed to the exterior of the inner wrap 95 spaced longitudinally a short distance from the end 103, as by a second row of stitching 104 forming a pocket opening 105 for hinge arm 85, as will be described.

The free or movable end of the outer wrap 96 carries a vertical adhering strip 107 positioned to be facing inwardly when the exterior strap 96 is wrapped in the direction indicated by the arrow 108 in FIG. 11. Horizontal adhering strips 109, 111 are located toward the fixed end 103 of exterior wrap 96 and are outwardly facing, positioned for attachment to the vertical adhering strip 107 when the wrap 96 is placed around the leg.

In order to reduce confusion on the part of the wearer of the wrap assembly, the various adhering strips can be color-coded. For example, the adhering strip 97 can be colored red, as well as the horizontal adhering strips 99, 101 on the opposite end of the inner wrap 95 so the wearer knows that these adhering strips go together. The wearer places the interior wrap 95 around his leg and then fastens the red vertical adhering strip 97 to the red horizontal adhering strips 99, 101. The outer wrap adhering strips 107, 109 and 111 can be another color, such as tan, such that the wearer knows that the vertical adhering strip 107 on the outer wrap 96 is meant to engage the horizontal adhering strips 109, 111 on the same wrap.

Figures 15, 16:
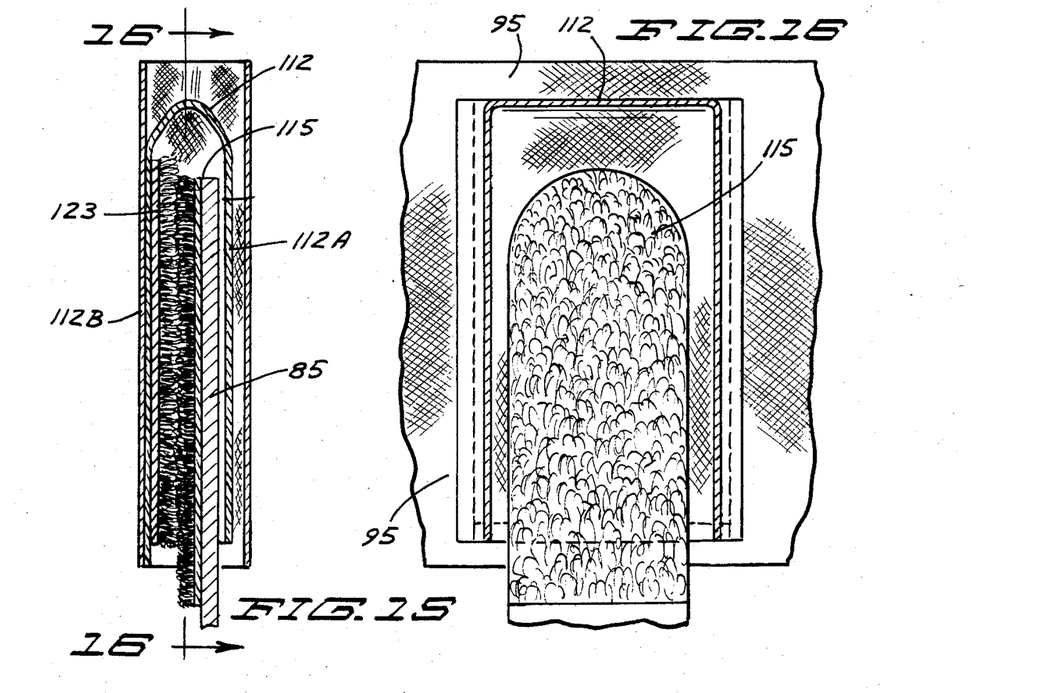
FIG. 15 is an enlarged sectional view of a portion of the leg wrap assembly of FIG. 12 taken along the line 15—15 thereof.
FIG. 16 is a sectional view of the portion of the leg wrap assembly of FIG. 15 taken along the line 16—16 thereof.

The relationship between the upper wrap assembly 80 and the attachment end of arm 85 is shown in FIGS. 12 through 16. Pocket opening 105 contains an open-ended pocket 112 fixed therein, as by being sewn to the interior end portion of outer wrap 96. As shown in the drawings, the end of arm 85 is insertable in the pocket 112. Referring to FIGS. 15 and 16, one interior side of the pocket 112 is lined with a strip of adhering material 113 suitably secured thereto as by gluing. One side of the attachment end of the arm 85 carries a second mating strip 115 of adhering material glued or suitably bonded thereon. The adhering materials 113, 115 are of the type made of synthetic material which adheres when pressed together and sold under the trademark Velcro. Upon insertion of the end of the arm 85 into the pocket 112, the adhering surfaces 113, 115 engage and securely hold the arm therein. The arm can be disengaged from the pocket 112 by moving the surface 115 away from the adhering surface 113 and then carefully sliding the arm 85 out of pocket 112 so as to avoid reengagement of the surfaces. When the arm 85 is engaged in the pocket 112 with the surfaces 113 and 115 in engagement, arm 85 is held securely in place with respect to the leg 77. The lower wrap assembly 81 is similar in construction to the upper wrap assembly 80 and similarly holds the attachment end of the second arm 92 in place whereby hinge assembly 82 is secured in stable relationship with respect to the knee 78.

In use of the knee brace 76, the first and second arms 85, 92 are inserted in the corresponding pockets of the upper and lower wrap assemblies 80, 81. The wrap assemblies 80, 81 are installed above and below the knee as shown in FIG. 9. The inner wrap 95 is wrapped in circumferential tension around the thigh with the proximal side thereof in contact with the leg. Vertical adhering strip 97 overlaps the horizontal adhering strips 99, 101. The length of the horizontal adhering strips 99, 101 permits proper adjustment of the wrap 95 according to leg size. Next, the outer wrap 96 is stretched in the opposite direction around the leg to a point where the vertical adhering strip 107 overlaps the horizontal adhering strips 109, 111 and is secured thereto with the outer wrap 96 in circumferential tension around the leg. The horizontal length of the adhering strips 109, 111 permits proper adjustment of the wrap about the leg in sufficient tension to securely hold the wrap in place. The lower wrap 81 is installed in the same fashion whereby the hinge assembly 82 is held in stable orientation with respect to the knee 78. Upon flexure of the knee 78, pivoting about the first, second and third hinge pins 88, 91, 93 permits the hinge to rotate about an axis which follows the normal axis of rotation of the knee. However, the knee is inhibited from abnormal rotation and twisting, extension, and is protected from lateral impact.

Referring to FIGS. 17 through 20, there is shown a support wrap assembly according to the invention indicated generally at 117 to provide generalized limb support and prevent injury or protect against aggravation of preexistent injury. Wrap assembly 117 is shown partially installed on the upper portion of a leg 118 in FIG. 17, and in side distal elevation, top plan, and side proximal elevational views in FIGS. 18, 19 and 20 respectively.

Figure 17:
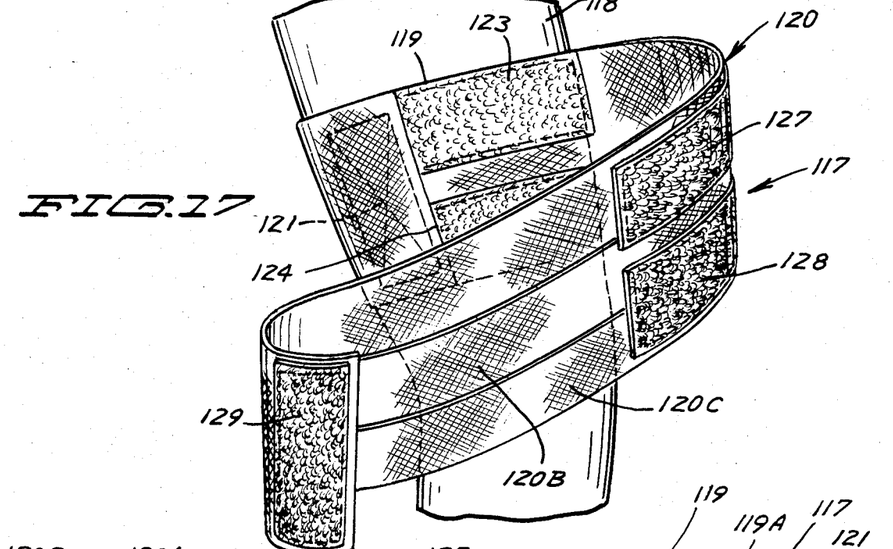
FIG. 17 is a side elevational view of a leg wrap assembly of the invention partially installed on a leg in location superior to the knee.
Figure 18:
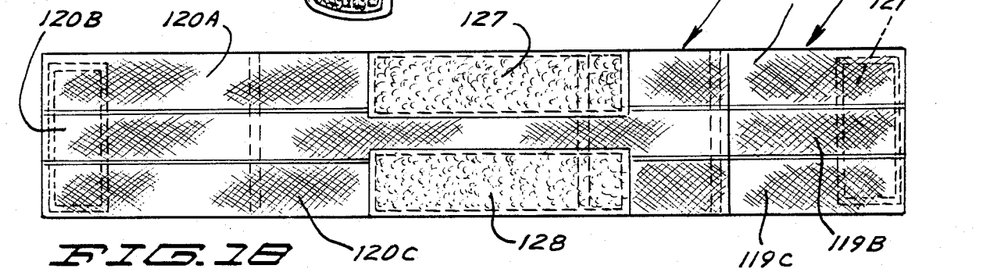
FIG. 18 is a side elevational view of the leg wrap assembly of FIG. 17 showing the distal side thereof.
Figure 19:
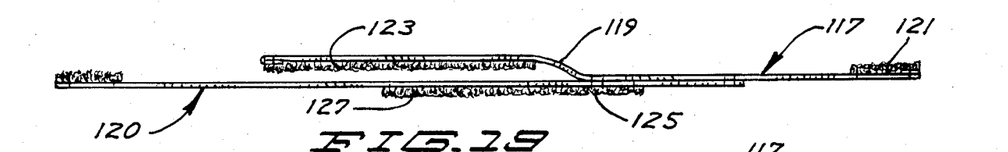
FIG. 19 is a top plan view of the leg wrap assembly of FIG. 18.

Wrap assembly 117 has an inner wrap 119 comprised as an elongate band of linearly elastic material for wrapping adjacent the leg, and an outer wrap 120 comprised as a second elongate band of linearly elastic material for wrapping around the inner wrap when installed on a leg. Inner wrap 119 has a vertical adhering or fastening strip 121 located on one end thereof positioned to be in facing relationship relative to the leg when the wrap is installed thereon, and a pair of horizontal adhering or fastening strips 123, 124 extending longitudinally from the opposite edge of the wrap 119 and facing outwardly so as to be in facing relationship to the fastening strip 121 when wrapped around a leg. The horizontal length of the fastening strips 123, 124, permits adjustment of the wrap upon the leg according to leg size.

One end of the outer band 120 is fixed at an intermediate location on the outside of the inner band 119, as by stitching 125, and carries first and second horizontal fastening strips 127, 128, positioned to be outward facing when installed on a leg. The opposite end of the outer wrap 120 carries a vertical fastening strip 129, such that the second wrap 120 can be wrapped around the leg in tension in covering relationship to the first wrap with the fastening strip 129 engaging a portion of the first and second horizontal fastening strips 127, 128. The horizontal length of the fastening strips 127, 128 permits adjustment of the position of the vertical fastening strip 129 according to the leg size.

In construction, each of the inner and outer wraps 119, 120 is comprised as a plurality of elongate longitudinal strips sewn together. For example, the wrap 119 is comprised of like parallel strips 119A, 119B, 119C, sewn together. Likewise, the outer wrap 120 is comprised of linear parallel strips 120A, 120B, 120C sewn together. The use of a plurality of parallel strips in forming a single band or wrap is advantageous in minimizing distortion of the composite wrap upon linear elongation.

Figure 20:
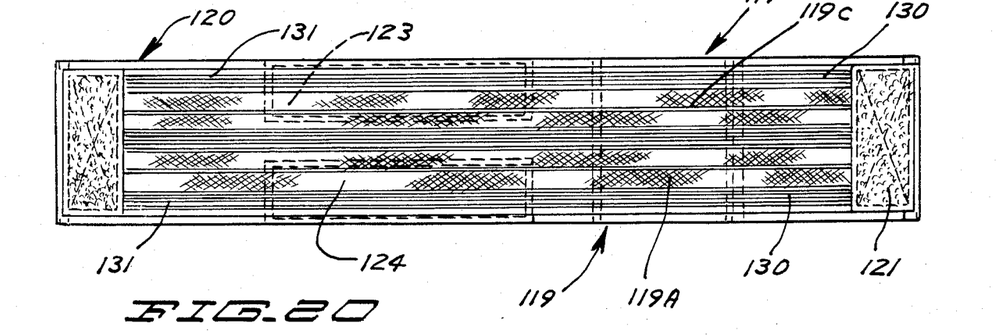
FIG. 20 is a side elevational view of the leg wrap assembly of FIG. 18 showing the opposite or proximal side thereof.

As shown in FIG. 20, the wraps 119, 120 can be provided with an impregnated or attached rubber material on the inwardly facing surfaces to prevent or retard slippage of the wrap which might otherwise occur upon activity of the wearer. Longitudinal rubber ribbons 130 are applied to the interior surfaces of the wrap strips 119A, B, C of wrap 119. Likewise, rubber ribbons 131 are centrally applied to the inwardly facing surfaces of the attached bands 120A, B, C of the wrap 120. The rubber ribbons stretch along with the band upon installation of the wrap assembly on a leg.

In use of the wrap assembly 117, the interior wrap 119 is first installed upon a leg over the portion to be protected. The end having horizontal fastening strips 123, 124 is placed on the leg, and the opposite end having the vertical fastening strip 121 is overlapped in tension and fastened at appropriate location according to the size of the leg. Mating fastening strips can be color-coded. The outer wrap 120 is wrapped in tension in the opposite circumferential direction around the leg locating the horizontal fastening strips 127, 128 in outwardly facing relationship for attachment to the vertical fastening strip 129. The rubber ribbons 130, 131 inhibit slippage of the wrap on the leg. The wrap is readily releasable and reusable.

While there have been shown and described certain embodiments of the invention, it will be understood that certain deviations can be had without departing from the scope and spirit of the invention.

The embodiments of the invention in which an exclusive property or privilege is claimed are defined as follows:

1. A knee brace to be worn on a leg and connected to the upper leg and lower leg in spanning relationship to the knee joint, comprising:
 a first leg pad shaped for positioning on a side of the upper leg above the knee, and means for securing the first leg pad to a leg;
 a second leg pad shaped for positioning on the side of a lower leg beneath the knee, and means for securing the second leg pad to the leg;
 a composite hinge assembly connecting the upper and lower leg pads, said hinge assembly having a plurality of rigid members, means pivotally connecting the rigid members together to form three pivot connections, a first of said pivot connections being located above the knee when the first and second leg pads are positioned on the leg and the leg is generally upright, a second of said pivot connections being located beneath the knee, and a third of said pivot connections being located vertically intermediate the first and second pivot connections to enable relative pivotal movement of the first and second leg pads about a composite horizontal axis of the hinge assembly generally corresponding to that of the knee joint;
 said rigid members of the hinge assembly including a first arm having a first end fixed to the first leg pad and a second end extended from the first end in the direction of the leg toward the knee;
 a second arm having a first end fixed to the second leg pad and a second end extended from the first end in the direction of the leg toward the knee;
 a first hinge plate having a flat proximal face and a distal face, a first T-shaped rib on the proximal face having a head and a stem, said head located proximate an edge of the first hinge plate facing interiorly of the direction of flexure of the knee, said stem extended transversely across the first hinge plate from the head, said head having interiorly curved upper and lower shoulders at the intersection with the stem;
 the second end of the first arm being pivotally connected to an upper portion of the first hinge plate to form the first of said pivot connections, said second end of the first arm having a downwardly facing outer edge that confronts the upper edge of the stem of the first rib to limit pivotal movement of the first arm and first hinge plate in rotational direction to straighten the knee, said second end of the first arm having a rearward exterior lower curved shoulder in facing relationship to the upper interior shoulder of the first rib and spaced to intercept it upon rotation of the first arm and first hinge plate to a preselected limit in direction of flexure of the knee;
 a second hinge plate having a flat proximal face and a distal face, a second T-shaped rib on the proximal face having a head and a stem, said head located proximate an edge of the second hinge plate facing interiorly of the direction of flexure of the knee, said stem extended transversely across the second hinge plate from the head, said head having interiorly curved upper and lower shoulders at the intersection with the stem;

the second end of the second arm being pivotally connected to a lower portion of the second hinge plate to form the second of said pivot connections;

said second end of the second arm having an upwardly facing outer edge that confronts the lower edge of the stem of the second T-shaped rib to limit pivotal movement of the second arm and second hinge plate in rotational direction to straighten the knee, said second end of the second arm having a rearward exterior upper curved shoulder in facing relationship to the lower interior shoulder of the second rib and spaced to intercept it upon rotation of the second arm and second hinge plate to a preselected limit in direction of flexure of the knee;

said first and second hinge plates disposed with proximal faces in facing relationship and pivotally connected to form the third of said pivot connections, each hinge plate having an edge in confronting relationship to the other edge of the stem of the opposite hinge plate to limit pivotal movement of the first and second hinge plates in rotational direction to straighten the knee, and an outwardly curved shoulder in facing relationship to the other interior shoulder of the rib of the other hinge plate and spaced to intercept it upon rotation of the first and second hinge plates to a preselected limit in direction of flexure of the knee.

2. The knee brace of claim 1 wherein: the outer ends of the first and second arms are laterally offset to laterally space the hinge assembly from the knee.

3. A knee brace to be worn on a leg secured to the upper leg and lower leg in spanning relationship to the knee joint, comprising:

upper leg wrap assembly engageable with the upper leg;

lower leg wrap assembly engageable with the lower leg;

a composite hinge assembly connecting the upper and lower leg wrap assemblies, said hinge assembly including a first arm having a first end fixed to the upper leg wrap assembly, and extended parallel to the upper leg toward the knee, a second end of the first arm pivotally connected to a first hinge plate at a location above the knee when the upper leg wrap assembly is engaged with the leg, a second hinge plate, said first and second hinge plates being pivotally connected, a second arm having a first end attached to the lower leg wrap assembly and extended parallel to the lower leg toward the knee, a second end of said second arm being pivotally connected to the second hinge plate for pivotal movement about an axis beneath the knee when the lower leg wrap assembly is engaged with the lower leg;

said first hinge plate having a flat proximal face and a distal face, a first T-shaped rib on the proximal face having a head and a stem, said head located proximate an edge of the first hinge plate facing interiorly of the direction of flecture of the knee, said stem extended transversely across the first hinge plate from the head, said head having interiorly curved upper and lower shoulders at the intersection with the stem;

the second end of the first arm being pivotally connected to an upper end of the first hinge plate, said second end of the first arm having a downwardly facing outer edge that confronts the upper edge of the stem of the first rib to limit pivotal movement of the first arm and the first hinge plate in rotational direction to straighten the knee, said second end of the first arm having a rearward exterior lower curved shoulder in facing relationship to the upper interior shoulder of the first rib and spaced to intercept it upon rotation of the first arm and first hinge plate to a preselected limit in direction of flexure of the knee;

said second hinge plate having a flat proximal face and a distal face, a second T-shaped rib on the proximal face having a head and a stem, said head located proximate an edge of the second hinge plate facing interiorly of the direction of flexure of the knee, said stem extended transversely across the second hinge plate from the head, said head having interiorly curved upper and lower shoulders at the intersection with the stem;

the second end of the second arm being pivotally connected to a lower end of the second hinge plate, said second end of the second arm having an upwardly facing outer edge that confronts the lower edge of the stem of the second T-shaped rib to limit pivotal movement of the second arm and second hinge plate in rotational direction to straighten the knee, said second end of the second arm having a rearward exterior upper curved shoulder in facing relationship to the lower interior shoulder of the second rib and spaced to intercept it upon rotation of the second arm and second hinge plate to a preselected limit in direction of flexure of the knee;

said first and second hinge plates disposed with proximal faces in facing relationship and pivotally connected, each hinge plate having an edge in confronting relationship to the other edge of the stem of the opposite hinge plate to limit pivotal movement of the first and second hinge plates in rotational direction to straighten the knee, and an outwardly curved shoulder in facing relationship to the other interior shoulder of the rib of the other hinge plate and spaced to intercept it upon rotation of the first and second hinge plates to a preselected limit in direction of flexure of the knee.

4. The knee brace of claim 3 wherein: the second ends of the first and second arms are laterally offset to laterally space the hinge assembly from the knee.

5. The knee brace of claim 4 wherein: said upper and lower leg wrap assemblies each include an inner elastic leg wrap circumferentially extendible around the leg, fastening means on first and second ends of the inner leg wrap to fasten it with respect to the leg; an outer elastic leg wrap having an end fixed to the inner leg wrap, and another end extendible around the inner leg wrap, means for attachment of the ends of the outer wrap; and pocket means for receipt of the first end of an arm.

6. The knee brace of claim 3 wherein: a first of said wrap assemblies includes an inner elongate circumferentially elastic wrap extendible around a leg, means on first and second ends of the inner wrap for releasably fastening the first and second ends together; an outer elongate circumferentially elastic wrap having one end fixed to an intermediate portion of the inner wrap and the other end extendible around the leg and the inner wrap, means on the ends of the outer wrap for releasably fastening them together; and a pocket fixed to one of said wraps for receipt of the first end of an arm.

7. The knee brace of claim 6 wherein: the other of said wrap assemblies is substantially, identical to the first.

8. The knee brace of claim 7 wherein: said upper wrap assembly has a first pocket, said first end of the first arm located in the first pocket, and means releasably securing the first end of the first arm in said first pocket; said lower wrap assembly having a second pocket, said first end of the second arm located in the second pocket, and means releasably securing the first end of the second arm in said second pocket.

9. The knee brace of claim 8 including: releasable adhering material located in the first pocket and on the first end of the first arm to releasably hold the first end of the first arm in said first pocket; and releasable adhering material located in the second pocket and on the first end of the second arm to releasably hold the first end of the second arm in the second pocket.

10. The knee brace of claim 6 wherein: a first end of the inner wrap has inwardly facing vertical fastening strip, the second end of the inner wrap having outwardly facing horizontal fastening strip for wrapping the first end of the wrap around a leg in a first direction to overlap the second end and releasably secure the first end to the second end; a first end of the exterior wrap having a vertical inwardly facing fastening strip, said second end fixed to the inner wrap having a horizontal outwardly facing fastening strip and positioned so that the first end is wrapped around the leg in a second direction to overlap the second end for releasably fastening the first and second ends.

11. The knee brace of claim 10 wherein: said fastening strips are comprised of synthetic material that adheres when pressed together.

12. The knee brace of claims 11 wherein: said fastening strips on the inner wrap are one color and said fastening strips on the outer wrap are a different color.

13. A knee brace to be worn on a leg secured to the upper leg and lower leg in spanning relationship to the knee joint, comprising:
upper leg wrap assembly engagable with the upper leg;
lower leg wrap assembly engagable with the lower leg;
composite hinge assembly means connecting the upper and lower leg wrap assemblies, said hinge assembly means including a first arm having a first end fixed to the upper leg wrap assembly, and a second arm with a first end connected to the lower leg wrap assembly, and means hingedly connecting the second ends of the first and second arms;
each of said wrap assemblies including an inner elongate circumferentially elastic wrap extendible around a leg, outwardly facing fastening means on a first end and inwardly facing fastening means on the second end of the inner wrap for releasably fastening the first and second ends together by holding the first end in position and wrapping the second end around the leg in a first circumferential direction to a position where the first and second fastening means overlap;
an outer elongate circumferentially elastic wrap having a first end fixed to an intermediate outside portion of the inner wrap and a second end extendible around the leg and the inner wrap in a second opposite circumferential direction, outwardly facing fastening means on the first end and inwardly facing fastening means on the second end of the outer wrap for releasably fastening them together upon wrapping the outer wrap around the leg in said second circumferential direction to a position where the first and second fastening means overlap.

14. The knee brace of claim 13 wherein: said fastening means are comprised of strips of synthetic material that adhere when pressed together.

15. The knee brace of claim 13 wherein: the first end of the inner wrap has inwardly facing vertical fastening strip, the second end of the inner wrap having outwardly facing horizontal fastening strip for adjustably wrapping the first end of the wrap around a leg in said first direction to overlap the second end and releasably secure the first end to the second end; the first end of the exterior wrap having a vertical inwardly facing fastening strip, said second end fixed to the inner wrap having a horizontal outwardly facing fastening strip and positioned so that the first end is adjustably wrapped around the leg in a second direction to overlap the second end for releasably fastening the first and second ends.

16. The knee brace of claim 15 wherein: said fastening strips are comprised of synthetic material that adheres when pressed together.

17. The knee brace of claim 16 wherein: said fastening strips on the inner wrap are one color and said fastening strips on the outer wrap are a different color.

18. The knee brace of claim 13 wherein: said upper wrap assembly has a first pocket, said first end of the first arm located in the first pocket, and means releasably securing the first end of the first arm in said first pocket; said lower wrap assembly having a second pocket, said first end of the second arm located in the second pocket, and means releasably securing the first end of the second arm in said second pocket.

19. The knee brace of claim 18 including: releasable adhering material located in the first pocket and on the first end of the first arm to releasably hold the first end of the first arm in said first pocket; and releasable adhering material located in the second pocket and on the first end of the second arm to releasably hold the first end of the second arm in the second pocket.

* * * * *